(12) United States Patent
Hiyama et al.

(10) Patent No.: US 7,981,638 B2
(45) Date of Patent: Jul. 19, 2011

(54) MOLECULE TRANSFER/DELIVERY SYSTEM

(75) Inventors: Satoshi Hiyama, Yokohama (JP); Yuki Moritani, Yokohama (JP); Tatsuya Suda, Fallbrook, CA (US); Yasushi Isogawa, Tokyo (JP); Kazuo Sutoh, Tokyo (JP)

(73) Assignees: NTT DoCoMo, Inc., Tokyo (JP); The University of Tokyo, Tokyo (JP)

( * ) Notice: Subject to any disclaimer, the term of this patent is extended or adjusted under 35 U.S.C. 154(b) by 1061 days.

(21) Appl. No.: 11/551,041

(22) Filed: Oct. 19, 2006

(65) Prior Publication Data

US 2009/0156791 A1 Jun. 18, 2009

(30) Foreign Application Priority Data

Oct. 21, 2005 (JP) ................................ 2005-307880

(51) Int. Cl.
*C12P 19/34* (2006.01)

(52) U.S. Cl. .................................. 435/91.1; 435/287.3

(58) Field of Classification Search ........................ None
See application file for complete search history.

(56) References Cited

U.S. PATENT DOCUMENTS

| 2003/0235854 A1* | 12/2003 | Chan et al. ....................... | 435/6 |
| 2009/0035751 A1* | 2/2009 | He et al. ............................ | 435/6 |

FOREIGN PATENT DOCUMENTS

| DE | 103 38 657 A1 | 3/2005 |
| WO | WO 2004/096831 A2 | 11/2004 |

OTHER PUBLICATIONS

Yong-Zhong Du, et al., "Motor protein nano-biomachine powered by self-supplying ATP", Chem. Commun., XP-002431642, No. 16, 2005, pp. 2080-2082.
Henry Hess, et al., "Powering Nanodevices with Biomolecular Motors", Chem. Eur. J., XP-001203432, vol. 10, No. 9, 2004, pp. 2110-2116.
Henry Hess, et al., "Molecular shuttles based on motor proteins: active transport in synthetic environments", Reviews in Molecular Biotechnology, XP-002300012, vol. 82, No. 1, 2001, pp. 67-85.
Sujatha Ramachandran, et al., "Selective Loading of Kinesin-Powered Molecular Shuttles with Protein Cargo and its Application to Biosensing", Small, XP-002431644, vol. 2, No. 3, 2006, pp. 330-334.
Yuichi Hiratsuka, et al., "Controlling the Direction of Kinesin-Driven Microtubule Movements along Microlithographic Tracks," Biophysical Journal, vol, 81, Sep. 2001, pp. 1555-1561.
Henry Hess, et al., "Light-Controlled Molecular Shuttles Made from Motor Proteins Carrying Cargo on Engineered Surfaces," Nano Letters, vol. 1, No. 5, 2001, pp. 235-239.
Kazuaki Kato, et al., "Mircotubule-Cyclodextrin Conjugate: Functionalization of Motile Filament with Molecular Inclusion Ability," Bioscience, Biotechnology, and Biochemistry, vol. 69, No. 3, Mar. 2005, pp. 646-648.

\* cited by examiner

*Primary Examiner* — James S Ketter
(74) *Attorney, Agent, or Firm* — Oblon, Spivak, McClelland, Maier & Neustadt, L.L.P.

(57) ABSTRACT

A molecule transfer and delivery system includes a loading zone (50) for loading a targeted cargo molecule (30) on a carrier molecule (20) making use of a hybridization nature of nucleotides, and an unloading zone (40) for unloading the targeted cargo molecule from the carrier molecule making use of the strand exchange nature of the nucleotides. Towing nucleotide chains including the first single-stranded nucleotides (21) with the first length are bound to the carrier molecule, and the second single-stranded nucleotides (31) with the second length longer than the first length are bound to the targeted cargo molecule. The third single-stranded nucleotides (41) with the same length as the second single-stranded nucleotides are bound to the unloading zone.

18 Claims, 5 Drawing Sheets

```
                        SEQUENCE LISTING

<160> NUMBER OF SEQ ID NOS: 8

<210> SEQ ID NO 1
<211> LENGTH: 12
<212> TYPE: DNA
<213> ORGANISM: artificial
<220> FEATURE:
<223> OTHER INFORMATION: synthetic 12-base ss-DNA 21, 5' to 3' sequence

<400> SEQUENCE: 1
tactttattt tg                                                         12

<210> SEQ ID NO 2
<211> LENGTH: 32
<212> TYPE: DNA
<213> ORGANISM: artificial
<220> FEATURE:
<223> OTHER INFORMATION: synthetic 32-base ss-DNA 31A (shown 5' to 3')

<400> SEQUENCE: 2
taaacaaaat gaaataaaac caaaataaag ta                                   32

<210> SEQ ID NO 3
<211> LENGTH: 32
<212> TYPE: DNA
<213> ORGANISM: artificial
<220> FEATURE:
<223> OTHER INFORMATION: synthetic ss-DNA 41A, 5' to 3'

<400> SEQUENCE: 3
tactttattt tggttttatt tcattttgtt ta                                   32

<210> SEQ ID NO 4
<211> LENGTH: 32
<212> TYPE: DNA
<213> ORGANISM: artificial
<220> FEATURE:
<223> OTHER INFORMATION: synthetic ss-DNA 31A (shown 5' to 3')

<400> SEQUENCE: 4
taaacaaaat gaaataaaac caaaataaag ta                                   32
```

```
<210> SEQ ID NO 5
<211> LENGTH: 32
<212> TYPE: DNA
<213> ORGANISM: artificial
<220> FEATURE:
<223> OTHER INFORMATION: synthetic ss-DNA 31B (shown 5' to 3')

<400> SEQUENCE: 5
attttggtta ttttactttt caaaataaag ta                                32

<210> SEQ ID NO 6
<211> LENGTH: 32
<212> TYPE: DNA
<213> ORGANISM: artificial
<220> FEATURE:
<223> OTHER INFORMATION: synthetic ss-DNA 41A

<400> SEQUENCE: 6
tactttattt tggttttatt tcattttgtt ta                                32

<210> SEQ ID NO 7
<211> LENGTH: 32
<212> TYPE: DNA
<213> ORGANISM: artificial
<220> FEATURE:
<223> OTHER INFORMATION: synthetic ss-DNA 41B

<400> SEQUENCE: 7
tactttattt tgaaaagtaa aataaccaaa at                                32

<210> SEQ ID NO 8
<211> LENGTH: 24
<212> TYPE: DNA
<213> ORGANISM: artificial
<220> FEATURE:
<223> OTHER INFORMATION: synthetic DNA containing 21a and 21b sequences
      (shown 5' to 3')
<220> FEATURE:
<221> NAME/KEY: misc_feature
<222> LOCATION: (1)..(12)
<223> OTHER INFORMATION: synthetic DNA sequence 21b
<220> FEATURE:
<221> NAME/KEY: misc_feature
<222> LOCATION: (13)..(24)
<223> OTHER INFORMATION: synthetic DNA sequence 21a

<400> SEQUENCE: 8
gttttatttc atcagcccac cgga                                         24
```

MOLECULE TRANSFER/DELIVERY SYSTEM

FIELD OF THE INVENTION

The present invention relates to a molecule transfer and delivery system for loading, transporting, and unloading of the targeted cargo molecules in an autonomous fashion.

BACKGROUND OF THE INVENTION

It is known that gliding motion of microtubules or actin filaments can be observed along a microscopic channel patterned in a glass or plastic substrate, in which channel motor proteins such as kinesins or myosins are adsorbed. Such gliding motion occurs due to mutual interaction between the motor proteins adsorbed in the channel and the microtubules or the actin filaments. The microscopic channel can be formed using electron beam lithography or irradiation of ultraviolet rays. See, for example, Non-Patent Publication 1 listed below. It is also known that by biotinylating the surfaces of the gliding microtubules and by causing biotin-avidin bindings between the biotinylated microtubules and targeted cargo molecules (such as streptavidin coated microbeads), the targeted cargo molecules can be loaded on and transported by the gliding microtubules. See, for example, Non-Patent Publication 2 listed below.

Because it is well-known that biotin-avidin binding has remarkable strong affinity among biological bindings, it is inherently difficult to unload the cargo molecules from the gliding microtubules once the cargo molecules are loaded on the microtubules.

Meanwhile, a system concept for loading and unloading of targeted cargo molecules (guest molecules of cyclodextrins) on and from gliding microtubules in a reversible fashion is proposed. See, for example, Non-Patent Publication 3 listed below. Such a reversible loading/unloading operation is realized by biotinylating cyclodextrin that is able to include and release a guest molecule in a controlled manner and by conjugating the biotinylated cyclodextrin with a biotinylated microtubule via streptavidin. It is difficult, however, to operate this system autonomously without external control because some external stimulation (for example, irradiation of ultraviolet rays) has to be given to achieve controlled release of the guest molecule from cyclodextrin. This drawback causes further problems in that system control becomes complicated and the system scale becomes huge as a whole due to an external control system.

[Non-Patent Publication 1]
  Y. Hiratsuka, et al., "Controlling the Direction of Kinesin-driven Microtubule Movements along Microlithographic Tracks," Biophysical Journal, vol. 81, pp. 1555-1561, September 2001.

[Non-Patent Publication 2]
  H. Hess, et al., "Light-controlled Molecular Shuttles Made from Motor Proteins Carrying Cargo on Engineered Surfaces," Nano Letters, vol. 1, No. 5, pp. 235-239, 2001.

[Non-Patent Publication 3]
  K. Kato, et al., "Microtubule-cyclodextrin Conjugate: Functionalization of Motile Filament with Molecular Inclusion Ability," Bioscience, Biotechnology, and Biochemistry, vol. 69, No. 3, pp. 646-648, March 2005.

SUMMARY OF THE INVENTION

Therefore, the embodiments of the present invention provide an autonomous molecule transfer/delivery system that can load targeted cargo molecules on gliding carrier molecules, transport them to a designated destination, and unload the transported cargo molecules from the carrier molecules at the destination in an autonomous fashion.

To realize the system, single-stranded towing nucleotides are bonded biochemically to a carrier molecule (such as a microtubule or an actin filament) in such a manner that the gliding ability of the carrier molecule is not prevented. On the other hand, single-stranded loading nucleotides which are longer than the towing nucleotides are bonded biochemically to a targeted cargo molecule. The single-stranded towing nucleotides and the single-stranded loading nucleotides are designed so as to be partially complementary to each other and to form double-stranded nucleotides.

With this arrangement, when the carrier molecule with the single-stranded towing nucleotides passes by the targeted cargo molecule with the single-stranded loading nucleotides in its gliding motion, double stranding reaction (hybridization) occurs between these two single-stranded nucleotides, and consequently the targeted cargo molecule is loaded on the carrier molecule. The hybridization is a biochemical reaction naturally caused by transition of the energy state (the double-stranded nucleotide is more stable than a single-stranded nucleotide), and it does not require external control. The carrier molecule-targeted cargo molecule conjugate glides on the immobilized motor proteins along the patterned channel toward the destination.

At the destination, single-stranded unloading nucleotides are bonded to the channel surface. The single-stranded unloading nucleotides have the same length as the single-stranded loading nucleotides of the targeted cargo molecule, and are complete complementary with respect to the loading nucleotides so as to produce a double strand. When the carrier molecule towing the targeted cargo molecule passes through the destination in its gliding motion, more stable double stranding reaction (hybridization) occurs between the single-stranded unloading nucleotide fixed at the destination and the single-stranded loading nucleotide of the targeted cargo molecule transported by the carrier molecule. As a result, the original double strand between the targeted cargo molecule and the carrier molecule is undone (dehybridized), and the targeted cargo molecule is unloaded from the carrier molecule at the destination due to the strand exchange.

In one aspect of the invention, a molecule transfer and delivery system includes:
(a) a loading zone for loading a targeted cargo molecule on a carrier molecule making use of a hybridization nature of nucleotides; and
(b) an unloading zone for unloading the targeted cargo molecule from the carrier molecule, making use of the strand exchange nature of the nucleotides.

In a preferred example, towing nucleotide chains including the first single-stranded nucleotides with the first length are bonded to the carrier molecule, and the second single-stranded nucleotides with the second length longer than the first length are bonded to the targeted cargo molecule, thereby loading the targeted cargo molecule on the carrier molecule by formation of a double strand between the first single-stranded nucleotide and the second single-stranded nucleotide at the loading zone.

In another preferred structure, the system further includes a channel extending between the loading zone and the unloading zone, to which channel motor proteins are adsorbed. The carrier molecule glides over the immobilized motor proteins along the channel.

In still another preferred structure, the third single-stranded nucleotides with the same length as the second single-stranded nucleotides are bonded to the unloading zone.

In yet another preferred example, the nucleotide chain bonded to at least one of the carrier molecule, the targeted cargo molecule, and the unloading zone has a double-stranded base portion and a single-stranded end portion (sticky end). In this case, the melting temperature of the double-stranded base portion is higher than the melting temperature for dehybridizing a double strand to be formed using the single-stranded end portion.

In the second aspect of the invention, a molecule transferring and delivering method is provided. The method includes the steps of:
(a) loading a targeted cargo molecule on a carrier molecule making use of a hybridization nature of nucleotides; and
(b) unloading the targeted cargo molecule from the carrier molecule at a destination making use of the strand exchange nature of the nucleotides.

Preferably, the method may include further steps of:
(c) bonding towing nucleotide chains including the first single-stranded nucleotides with the first length to the carrier molecule;
(d) allowing the carrier molecule to glide over the immobilized motor proteins along a channel extending to the destination;
(e) introducing a targeted cargo molecule into the channel, the targeted cargo molecule having the second single-stranded nucleotides with the second length longer than the first length;
(f) loading the targeted cargo molecule on the carrier molecule making use of formation of a double strand between the first single-stranded nucleotide and the second single-stranded nucleotide; and
(g) transporting the targeted cargo molecule to a destination along the channel.

In a preferred example, the targeted cargo molecule is unloaded from the carrier molecule at the destination upon formation of a double strand between a third single-stranded nucleotide fixed to the destination and a non-contributing portion of the second single-stranded nucleotide that does not contribute to the formation of the double strand with the first single-stranded nucleotide.

With the above-described system and method, a series of operations of loading targeted cargo molecules on carrier molecules that are in gliding motion, transporting the targeted cargo molecules to a destination, and unloading the targeted cargo molecules at the destination can be carried out in an autonomous fashion without external control.

BRIEF DESCRIPTION OF THE DRAWINGS

Other features and advantages of the invention will become more apparent from the following detailed description when read in conjunction with the accompanying drawings, in which.

DETAILED DESCRIPTION OF THE PREFERRED EMBODIMENT

The preferred embodiments of the present invention are described below in conjunction with the attached drawings. In the embodiments, microtubules are used as carrier molecules, single-stranded deoxyribo nucleic acids (ss-DNAs) are used as the single-stranded nucleotides, and kinesins are used as motor proteins for purposes of illustration and not limitation.

Figure 1:
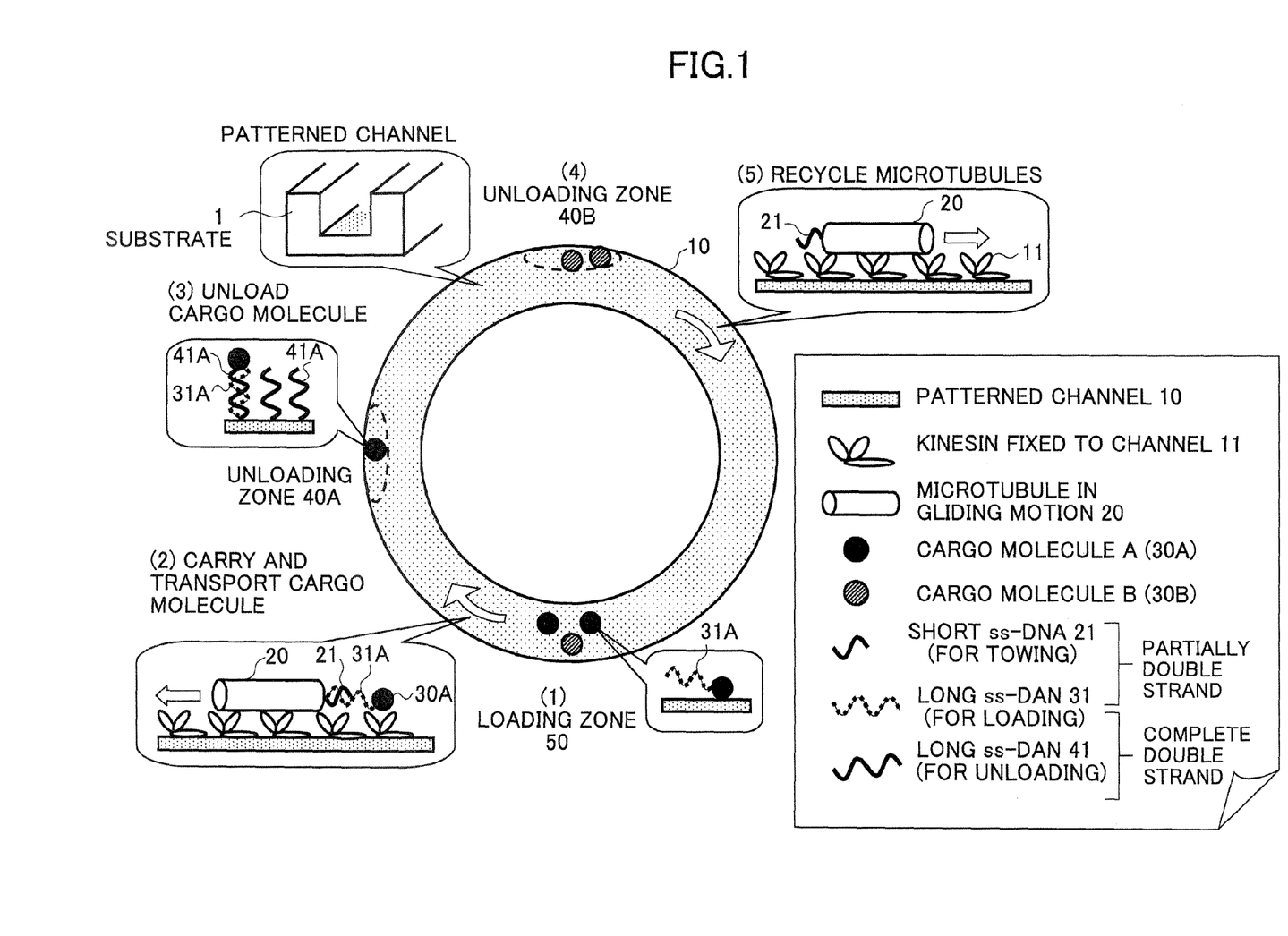
FIG. 1 is a schematic diagram of a molecule transfer/delivery system according to an embodiment of the invention.

FIG. 1 illustrates the overall structure of a molecule transfer/delivery system according to an embodiment of the invention. The system includes a patterned channel (flow path) 10, motor proteins (kinesins) 11 adsorbed to the surface of the patterned channel 10, carrier molecules (microtubules) 20 gliding over the immobilized motor proteins 11 along the patterned channel 10, a loading zone 50 for loading targeted cargo molecules 30 on the carrier molecules 20, and unloading zones 40 for unloading the targeted cargo molecules 30 from the carrier molecules 20.

Short single-stranded nucleotides (referred to as "short ss-DNAs" or "the first ss-DNAs") 21 are bonded to each of the microtubules 20 serving as the carrier molecule. These short ss-DNAs 21 serve as towing nucleotides.

Single-stranded nucleotides (referred to as "long ss-DNAs" or "the second ss-DNAs") 31 longer than the short ss-DNAs 21 are bonded to each of the targeted cargo molecules 30. Each long ss-DNA 31 is designed such that a part of the long ss-DNA 31 is complementary with respect to the short ss-DNA 21 of the microtubule 20 to form a partially double strand.

The third single-stranded nucleotides (referred to as "long ss-DNAs") 41 are bonded to the unloading zone 40. Each the third single-stranded nucleotide 41 has the same length as the second ss-DNA 31 of the targeted cargo molecule 30 and is complete complementary with respect to the second ss-DNA 31 so as to form a complete double strand.

The patterned channel (flow path) 10 is fabricated by delineating a fine pattern of a nanometer or micrometer scale on the glass or plastic substrate 1 by irradiation of ultraviolet rays or direct drawing using electron beam. In the example shown in FIG. 1, only a single circled channel 10 is depicted for purposes of simplification; however, the invention is not limited to this example and the channel can be patterned into a desired shape and layout.

Kinesins 11 serving as motor proteins are applied and adsorbed to the patterned channel 10. Kinesins 11 may be of a wild type purified from a porcine brain or the like, or of a recombinant type purified from *E. Coli* expressing kinesin plasmid derived from a drosophila or a rat. There are many methods for adsorbing kinesins 11 onto the patterned channel 10. For example, when using recombinant-type kinesins 11, the tail parts of kinesins 11 are biotinylated, while proteins, such as bovine serum albumin (BSA), easy to adsorb to the surface of the patterned channel 10 are also biotinylated. The biotinylated kinesins 11 can be immobilized to the biotinylated channel surface via streptavidins. The patterned channel is filled with aqueous solution in which adenosine triphosphate (ATP), magnesium ions, or other components required to activate the kinesins 11 are dissolved.

Short ss-DNAs (the first ss-DNAs) 21 are bonded biochemically to each of the microtubules 20 that glide over the kinesins 11 adsorbed to the patterned channel 10. There are many methods for bonding the short ss-DNAs 21 to the microtubule 20. For example, the carboxyl groups of a microtubule 20 can be bound chemically to the 5'-end-aminated or 3'-end-aminated short ss-DNAs 21 using a cross-linking agent, or the amino groups of a microtubule 20 can be bound chemically to the 5'-end-thiolated or the 3'-end-thiolated short ss-DNAs 21 using a cross-linking agent. Another alternative is to bind the biotinylated microtubule 20 to the 5'-end-biotinylated or the 3'-end-biotinylated short ss-DNAs 21 via streptavidin.

The strand length of the first ss-DNA 21 is arbitrary, and it may have twelve bases. The base sequence of the ss-DNA 21 is also arbitrary, but it is desired to select the base sequence so as to prevent a closed loop (such as a hairpin loop structure) from being produced and to allow double stranding reaction (hybridization) to occur at room temperature.

The second ss-DNAs 31 are bonded biochemically to the targeted cargo molecule 30. The second ss-DNA 31 is longer than the first ss-DNA 21 bound to the microtubule 20 and partially complementary with respect to the first ss-DNA 21 to form a double strand. In the embodiment, the strand length of the second ss-DNA 31 is 32 bases. To bond the targeted cargo molecule 30 to the second ss-DNAs 31, a cross-linking agent or biotin-avidin bindings may be used as in the biochemical bindings between the microtubule 20 and the first ss-DNAs 21.

The targeted cargo molecule 30 may be an artificial composition or one derived from a living body. In FIG. 1, two types of targeted cargo molecules 30A and 30B are loaded on microtubules 20 and unloaded at the associated unloading zones 40A and 40B, respectively. Each of the targeted cargo molecules 30A and 30B is bonded to the associated one of long ss-DNAs 31A and 32B with different base sequences.

The targeted cargo molecules 30 with the first ss-DNAs 31 are introduced to the loading zone 50 arranged along the patterned channel 10 by, for example, external injection or dropping. Although in FIG. 1 only a single loading zone 50 is illustrated, two or more loading zones may be provided along the patterned channel. When the microtubule 20 with the short first ss-DNAs 21 passes near the targeted cargo molecule 30 with the long second ss-DNAs 31 in its gliding motion, double stranding reaction (hybridization) occurs between the first ss-DNA 21 and the second ss-DNA 31, and the targeted cargo molecule 30 is loaded on and towed by the microtubule 20.

Figure 2:
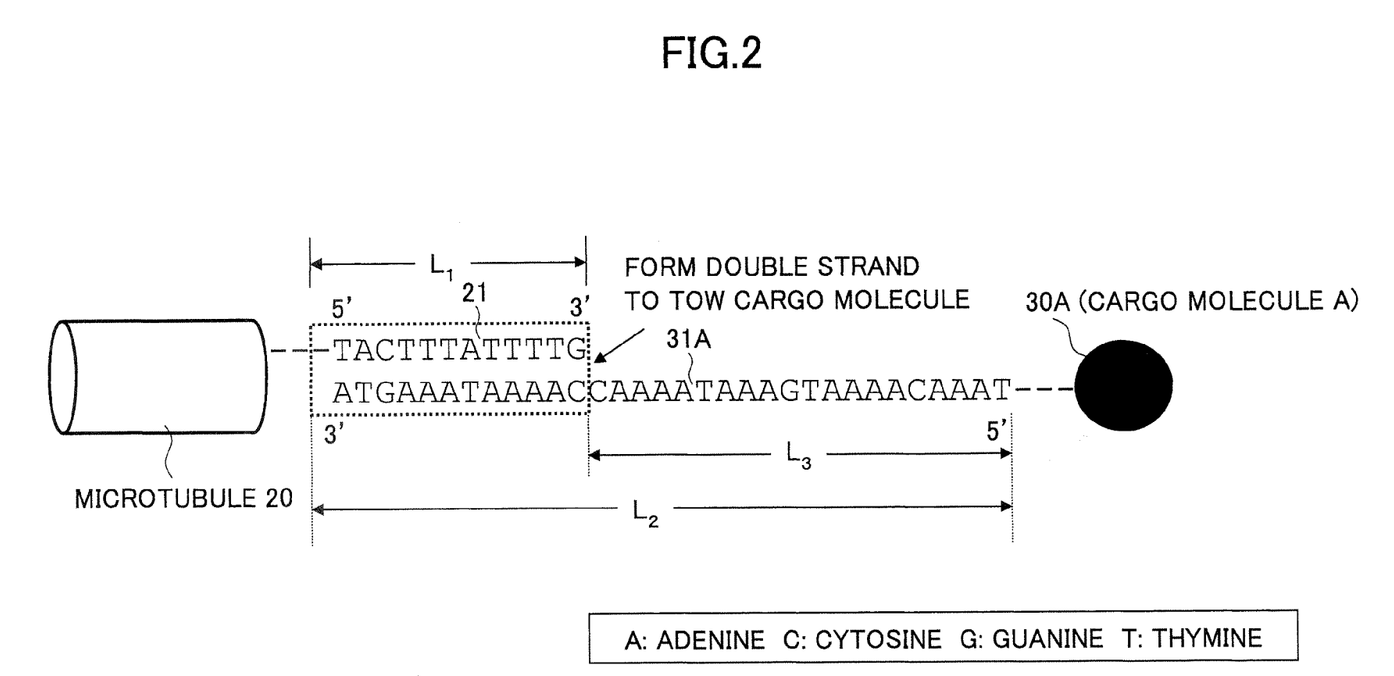
FIG. 2 illustrates an example of the targeted cargo molecule loaded on a carrier molecule (microtubule) by double stranding reaction between the single-stranded nucleotide bonded to the targeted cargo molecule and the single-stranded nucleotide bonded to the microtubule. The upper polynucleotide depicted is 21 (SEQ ID NO: 1) and the lower polynucleotide depicted in 3' to 5' orientation is 31A (SEQ ID NO: 2)

FIG. 2 illustrates an example of the targeted cargo molecule 30A loaded on the microtubule 20. The 12 bases of the 12-base ss-DNA 21 bound to the microtubule 20 and the 12 bases of the 32-base ss-DNA 31A bound to the targeted cargo molecule 30A form a double strand to allow the targeted cargo molecule 30A to be loaded on the microtubule 20. The base sequences of the first ss-DNA 21 of the microtubule 20 and a part of the second ss-DNA 31A (for example, 12 bases at the 3' end) of the targeted cargo molecule 30A are designed such that adenine (A) and thymine (T) are paired and that guanine (G) and cytosine (C) are paired so as to form a complementary strand pair. The double stranding reaction (hybridization) occurring between the first ss-DNA 21 and the second ss-DNA 31A is a natural biochemical reaction due to transition of the energy state to form a more stable double strand, and no external control is required.

It is necessary to set the gliding speed of the microtubule 20 slower than the reaction speed for producing the double strand. This can be achieved by adjusting the number or the length of the strands of the first ss-DNA 21 bound to the microtubule 20, and/or adjusting the ATP concentration of the solution.

The length L2 of the second ss-DNA 31A bound to the targeted cargo molecule 30A is longer than the length L1 of the first ss-DNA 21 bound to the microtubule 20 (L1<L2). In addition, the length L3 of the non-contributing part (that does not contribute to form a double strand with the first ss-DNA 21) of the second ss-DNA 31A is longer than the length L1 of the contributing part of the second ss-DNA 31A (L1<L3). This arrangement is employed to facilitate the double stranding reaction between the second ss-DNA 31A of the targeted cargo molecule 30A and the third ss-DNA 41A at the unloading zone 40A. This is described in more detail below.

Returning to FIG. 1, the microtubule 20 carrying the targeted cargo molecule 30A keeps the gliding motion on the kinesins 11 along the patterned channel 10 and transports the targeted cargo molecule 30A to the destination, which destination is the unloading zone 40A in this example. In the unloading zone 40A, the third ss-DNAs 41A with the same strand length as the second ss-DNAs 31A and with the sequence complete complementary with respect to those of the second ss-DNAs 31A so as to form a double strand are bound biochemically to the channel surface. In this example, the third ss-DNAs 41A are 32-base DNAs.

In bonding of the third ss-DNAs 41A to the channel 10, a DNA chip technology for arranging a number of DNA fragments in an array at high density can be applied. When the microtubule 20 that carries the targeted cargo molecule 30A passes through the destination (the unloading zone 40A) where the third ss-DNAs 41A are bound to the channel surface, double stranding reaction starts between the twenty 5'-end bases of the second ss-DNA 31A bound to the targeted cargo molecule 30A, which 20 bases are in the single strand without forming the double strand, and the third ss-DNA 41A bound to the unloading zone 40A. This reaction causes the twelve 3'-end bases of the second ss-DNA 31A to separate from the first ss-DNA 21 of the microtubule 20 to unfold the double strand, and to start forming another double strand with the third ss-DNA 41A bound to the destination (the unloading zone) 40A. As a result, the targeted cargo molecule 30A is unloaded from the microtubule 20.

This unloading operation (strand exchange) is achieved by the biochemical force urging the transition from the unstable energy state of the towing condition in which a single strand is left to the most stable energy state in which a complete double strand is formed, as well as by the physical force of kinesins for allowing the microtubules to glide.

Figure 3:
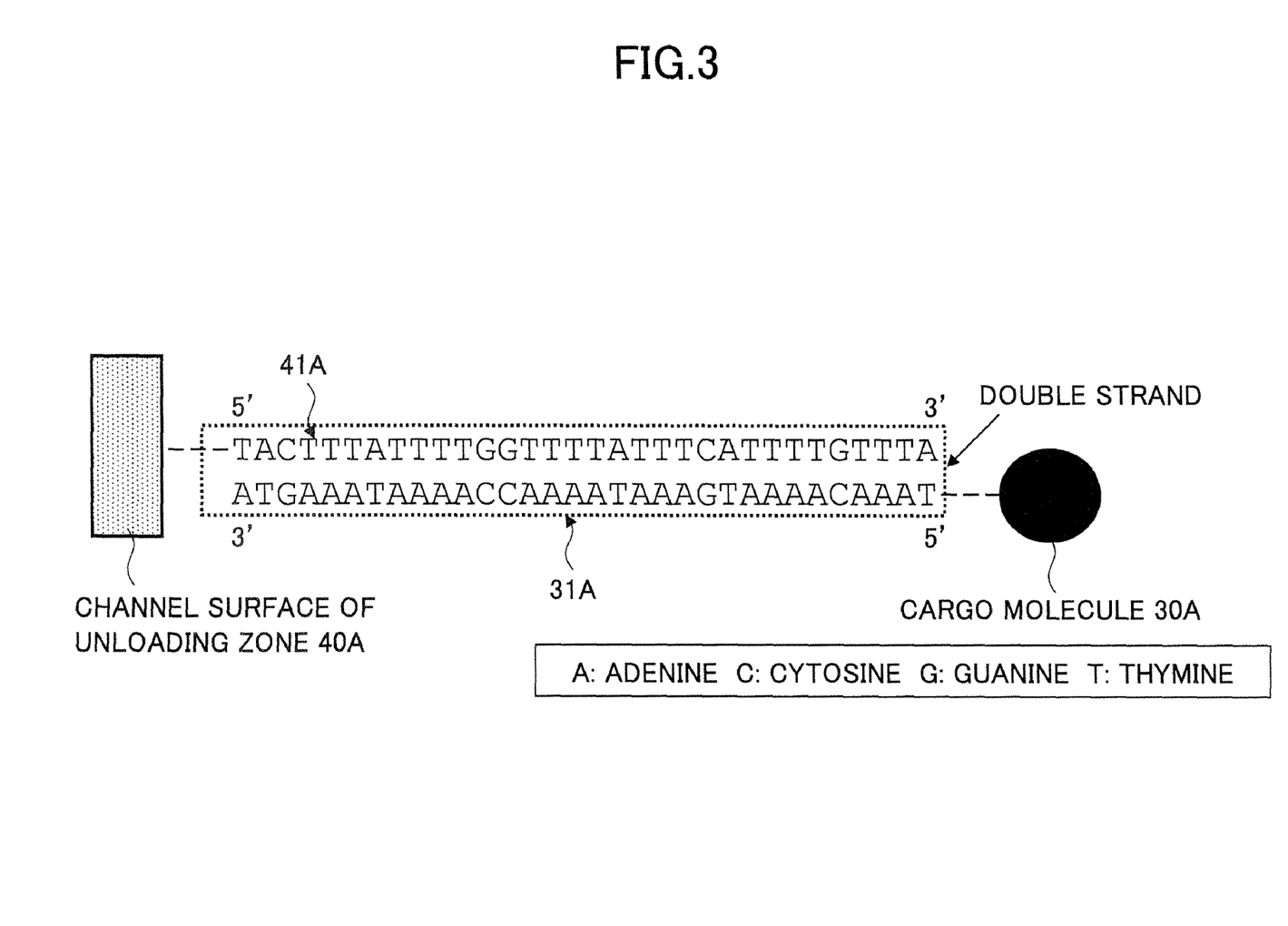
FIG. 3 illustrates an example of the targeted cargo molecule unloaded from the carrier molecule (microtubule) and received at the unloading zone by double stranding reaction between the single-stranded nucleotide of the targeted cargo molecule and the single-stranded nucleotide fixed at the unloading zone; the upper polynucleotide depicted in 5' to 3' orientation is 41A (SEQ ID NO: 3; the lower polynucleotide depicted in 3' to 5' orientation in 31A (SEQ ID NO: 4)

FIG. 3 illustrates an example of the targeted cargo molecule 30A unloaded from the microtubule 20 at the unloading zone 40A. The 32-base second ss-DNA 31A bound to the targeted cargo molecule 30A and the 32-base third ss-DNA 41A bound to the unloading zone 40A form a perfect double strand. This means that the targeted cargo molecule 30A is completely separated from the microtubule 20. The microtubule 20 that has unloaded the targeted cargo molecule 30A keeps its gliding motion, circulating along the patterned channel 10, and it can pick up a new targeted cargo molecule at the loading zone 50.

Two or more unloading zones (destinations) may be provided in the patterned channel 10, as illustrated in FIG. 1. In this case, it is desired to bind the third ss-DNAs (long ss-DNAs) with different base sequences to the channel surface at a different destination to unload a targeted cargo molecule of a different type.

Figure 4:
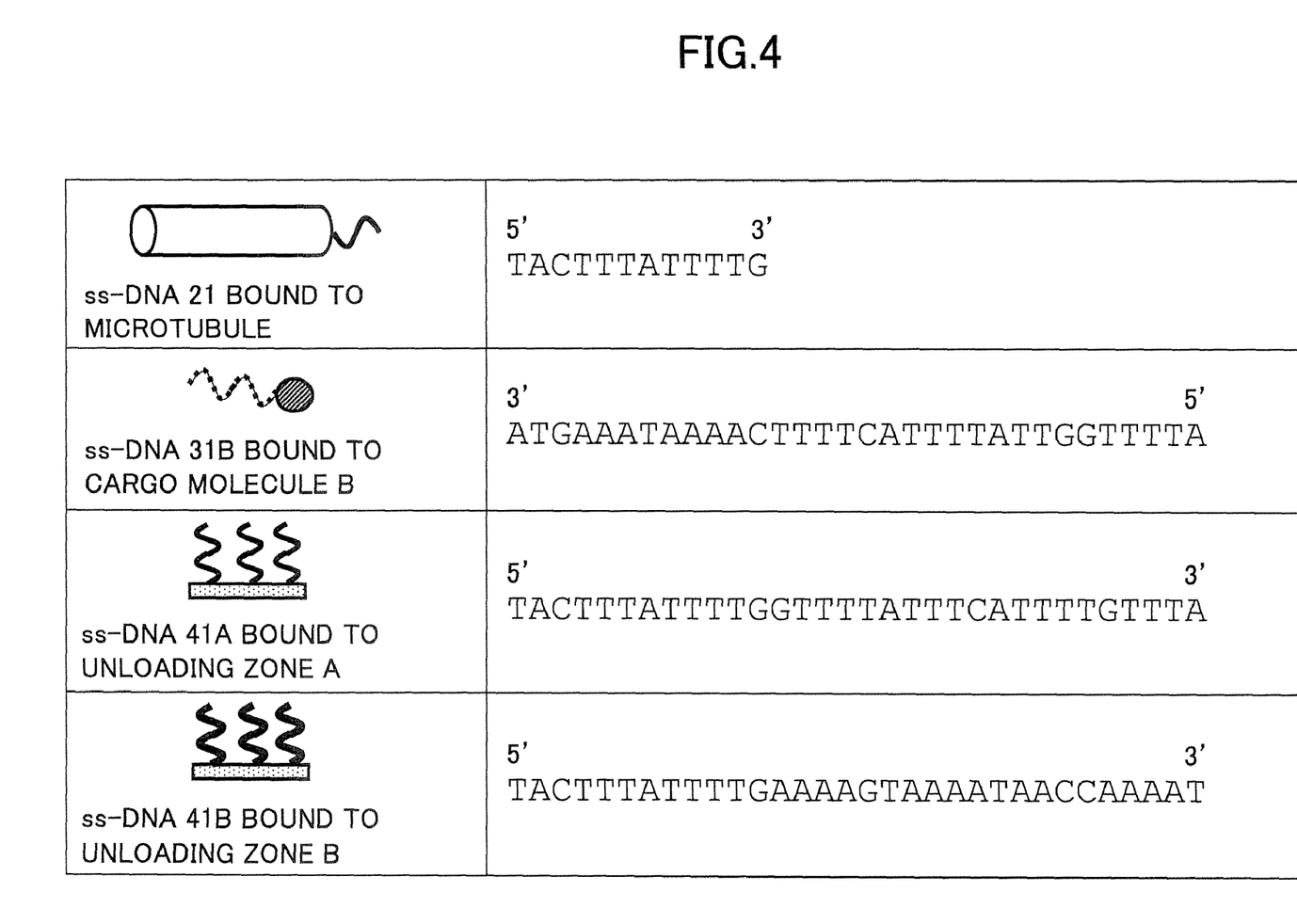
FIG. 4 illustrates examples of base sequences of single-stranded nucleotides used to sort different types of cargo molecules; the 21 (5' to 3'), 31B (3' to 5'), 41A (5' to 3') and 41B (5' to 3') polynucleotide sequences depicted correspond to SEQ ID NOS: 1, 5, 6 and 7, respectively.

FIG. 4 illustrates examples of second ss-DNA 31B and third ss-DNA 41B of different types used to unload a different targeted cargo molecule 30B from a microtubule 20 at a different unloading zone 40B. The base sequence of the second ss-DNA 31B bound to the targeted cargo molecule 30B is different from that of the second ss-DNA 31A bound to the targeted cargo molecule 30A. Accordingly, the second ss-DNA 31B is not complementary with respect to the third ss-DNA 41A bound to the unloading zone 40A and cannot form a double strand together with the ss-DNA 41A. For this reason, the microtubule 20 passes through the unloading zone 40A without unloading the targeted cargo molecule 30B. On the other hand, the second ss-DNA 31B bound to the targeted cargo molecule 30B is complementary with respect to the third ss-DNA 41B bound to the unloading zone 40B so as to form a double strand, and therefore, the targeted cargo molecule 30B is unloaded in the unloading zone 40B. In this arrangement, different types of targeted cargo molecules can be delivered to the associated destinations correctly and unloaded from the carrier molecules.

Although in the example shown in FIG. 4 a single type of microtubule with short ss-DNAs 21 bonded is used to transport different types of targeted cargo molecules 30A and 30B, microtubules 20A and 20B with different ss-DNAs 21A and ss-DNAs 21B with different base sequences, respectively, may be used. In this case, the two types of targeted cargo molecules can be sorted at the loading zone 50.

Figure 5:
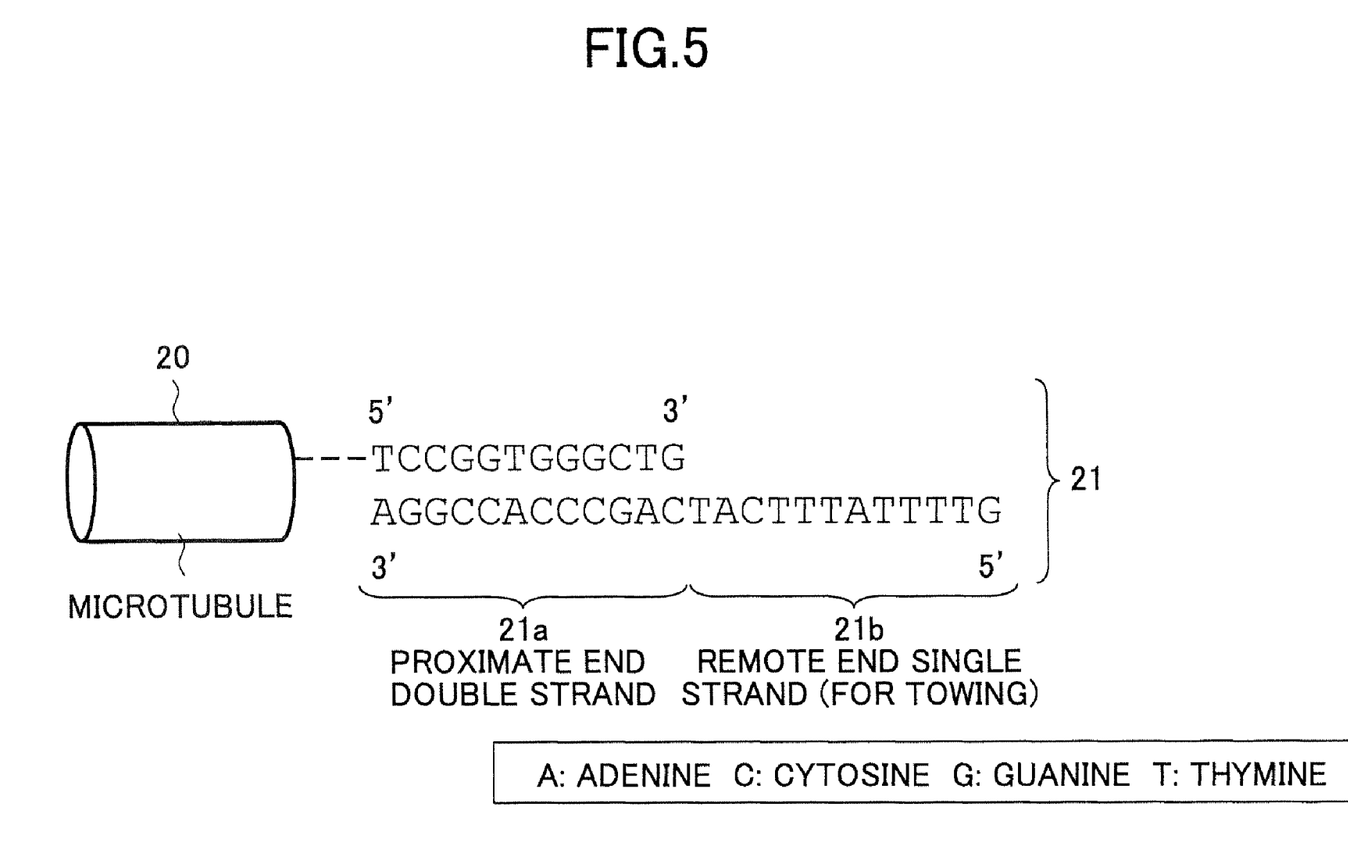
FIG. 5 illustrates modification of the towing nucleotide bonded to a carrier molecule (microtubule), the top sequence is SEQ ID NO: 1 (5' to 3') and the lower sequence depicted in 3' to 5' orientation is SEQ ID NO: 8.

FIG. 5 illustrates a modification of the towing nucleotide strand 21. In the previous example, single-stranded DNAs 21 are directly bound to microtubule 20. In this modification, the base portion of the towing strand bound to the microtubule 20 is double-stranded. For example, twelve bases arranged near the microtubule 20 are paired to form a double-stranded base portion (referred to as a "proximate-end double strand 21a"), and the remaining twelve bases define a single-strand end portion (referred to as a "remote-end single strand 21b"). The remote-end single strand 21b contributes to formation (hybridization) and separation (dehybridization) of the double strand formed by the reaction with the ss-DNA 31 bound to a targeted cargo molecule 30, thereby loading and unloading the targeted cargo molecule 30. The number of the base pairs in the proximate-end double strand 21a (arranged near the microtubule 20) can be adjusted to regulate the distance from the microtubule 20 to the remote-end single strand 21b which is used to form a double strand together with the ss-DNA 31 of the targeted cargo molecule 30.

In order to allow the ss-DNA 31 bound to the targeted cargo molecule 30 and the remote-end ss-DNA 21b bound to the microtubule 20 to react with each other to form the double strand, these two DNA strands have to approach to each other to a certain extent. Another requirement is that the ss-DNA 21 bound to the microtubule 20 has to be shorter than the ss-DNA 31 bound to the targeted cargo molecule 30 to conduct the unloading operation at the unloading zone. However; if the targeted cargo molecule 30 and the microtubule 20 are too close to each other, the motions of both the targeted cargo molecule 30 and the microtubule 20 are limited, and the gliding motion on the motor proteins (kinesins) 11 may be prevented.

In order to maintain an appropriate distance between the microtubule 20 and the targeted cargo molecule 30, the proximate-end of the towing strand (near the microtubule 20) is structured as a stable double strand 21a and the remote-end single strand 21b contributing to the hybridization with the targeted cargo molecule 30 is made an appropriate length (so as not to become too long). This arrangement is also advantageous because the ss-DNA 31 of the targeted cargo molecule 30 does not have to be unnecessarily long. Because a single-stranded DNA is inherently unstable, it is undesirable to bind an excessively long ss-DNA.

As is known in the art, the reaction temperature for dehybridizing the DNA double strand, that is, the melting temperature Tm for causing thermal denaturation to separate the double-stranded DNA into single strands varies depending on the length of the DNA sequence and the content of guanine (G) and cytosine (C) in the DNA sequence. In FIG. 5, the total number of G and C is 2 among the twelve bases defining the remote-end single strand 21b, and therefore, the GC content is 17%. In this case, the melting temperature Tm is about 26 degrees Celsius.

Then, if the temperature of the solution supplied in the patterned channel 10 is around 25 degrees Celsius, which temperature is slightly lower than the melting temperature of 26 degrees Celsius, the targeted cargo molecule 30 can be towed to the unloading zone 40, and in addition, dehybridization of the double strand formed by the twelve 3'-end bases of the ss-DNA 31 of the targeted cargo molecule 30 and the remote-end single strand 21b of the microtubule 20 can easily occur at the unloading zone 40 upon formation of a double strand due to reaction between the twelve 5'-end bases of the ss-DNA 31 of the targeted cargo molecule 30 and the third ss-DNA (unloading ss-DNA) 41.

In fact, it is desired to design the base sequence such that the melting temperature Tm of the short ss-DNA 21 (or the remote-end single strand 21b) bound to the microtubule 20 becomes the room temperature (around 25 degrees Celsius). If the melting temperature is too high, proteins (including kinesins) denature, and if the melting temperature is too low, the microtubule is dissolved (depolymerized).

On the other hand, to maintain the double strand, the base sequence is designed so as to raise the melting temperature Tm. Because the proximate-end double strand 21a bound to the microtubule 20 (shown in FIG. 5) does not contribute to loading and unloading of the targeted cargo molecule, the sequence of the proximate-end 12 bases is designed such that the GC content becomes 75% and that Tm becomes around 50 degrees Celsius. This means that the proximate double strand 21a does not dehybridize unless the temperature of the solution supplied in the patterned channel 10 exceed 50 degrees Celsius.

By appropriately designing the base sequences of the proximate-end double strand 21a and the remote-end single strand 21b of the microtubule 20, the loading/transporting/unloading operations can be carried out in a reliable manner.

The combination of a double strand and a single strand illustrated in FIG. 5 is not limited to the application to the towing nucleotide bound to the carrier molecule, e.g., microtubule 20, but can be applied to the loading nucleotide 31 bound to a targeted cargo molecule and the unloading nucleotide 41 bound to the unloading zone 40. In other words, the nucleotide chains bound to at least one of the nucleotide chains bound to the carrier molecule 20, the targeted cargo molecule 30, and the unloading zone 40 have the above-described double strand and single strand combination (sticky end) structure.

Although the embodiments have been described using microtubules 20 as carrier molecules, kinesins as motor proteins, and ss-DNAs 21, 31 and 41 as single-stranded nucleotide, the invention is not limited to this example and many modifications and substitutions can be made.

For example, when a microtubule is used as a carrier molecule, dynein may be used as a motor protein. If actin filament is used as a carrier molecule, myosin can be used as a motor protein. In the latter case, ss-DNAs can be bound to the actin filament via gelsolin coupled to the plus end of the actin filament. A part or all of the single-stranded nucleotide bound to the carrier molecule 20, the targeted cargo molecule 30, and the unloading zone 40 may be single-stranded ribonucleic acids (ss-RNAs).

The present invention can also be applied to a molecular communication system using targeted cargo molecules as communication (information transfer) carriers. In this case, information to be transmitted is encoded in targeted cargo molecules at a transmission site for loading the targeted cargo molecules. Information can be encoded by combining and coupling synthetic DNA and native DNA to produce a single-stranded or double-stranded DNA having a base sequence corresponding to the content to be transmitted. Alternatively, a single-stranded or double-stranded DNA having a structure (such as a hairpin structure or a bulge structure) corresponding to the information to be transmitted. In the latter case, the hairpin structure may be mapped to digital data "0" and the bulge structure may be mapped to digital data "1". Besides the coding of artificial analogue and digital information, life information possessed by DNA itself or therapeutic genes of disordered cells may be used as information to be transmitted.

The targeted cargo molecules may be unloaded at each of functional components, such as a pump, a valve, a sensor, or a reactor, on a chemical IC chip. In this case, the invention can be applied to a biochemical analysis/synthesis system of a microchip type using targeted cargo molecules as reagents or samples, and the circuit can be designed by arranging the motor protein adsorbed channel to a desired pattern.

This patent application is based upon and claims the benefit of the earlier filing date of Japanese Patent Application No. 2005-307880 filed Oct. 21, 2005, the entire contents of which are hereby incorporated by reference.

What is claimed is:

1. A molecule transfer and delivery system comprising:
   a carrier molecule having a first single-stranded nucleotide;
   a target cargo molecule having a second single-stranded nucleotide;
   a loading zone configured to allow the targeted cargo molecule to be loaded on the carrier molecule by formation of a partial double strand between a segment of the first single-stranded nucleotide and a complementary segment of the second single-stranded nucleotide; and
   an unloading zone to which a third single-stranded nucleotide is bound, the unloading zone being configured to cause the target cargo molecule to be unloaded from the carrier molecule by formation of a complete double strand between the second single-stranded nucleotide and the third single-stranded nucleotide that is more stable than the partial double-strand formed between the first single-stranded nucleotide and the complementary segment of the second single-stranded nucleotide.

2. The molecule transfer and delivery system of claim 1, wherein:
   the first single-stranded nucleotides bound to the target cargo molecule has a first length and serves as a towing nucleotide chain;
   the second single-stranded nucleotides bound to the target cargo molecule has a second length longer than the first length of the first single-stranded nucleotide; and
   the target cargo molecule is loaded on the carrier molecule by formation of the partial double strand between the first single-stranded nucleotide and the second single-stranded nucleotide at the loading zone.

3. The molecule transfer and delivery system of claim 1, further comprising:

a patterned channel extending between the loading zone and the unloading zone, to which channel motor proteins are adsorbed;

wherein the carrier molecule glides over the immobilized motor proteins along the patterned channel.

4. The molecule transfer and delivery system of claim 2, wherein the third single-stranded nucleotides bound to the unloading zone has the same length as the second single-stranded nucleotides.

5. The molecule transfer and delivery system of claim 4, wherein the targeted cargo molecule is unloaded from the carrier molecule at the unloading zone upon formation of the complete double strand between the third single-stranded nucleotide and the second single-stranded nucleotide that have contributed to the formation of the partial double strand with the first single-stranded nucleotide.

6. The molecule transfer and delivery system of claim 1, wherein:

at least one of the carrier molecule, the targeted cargo molecule, and the unloading zone has a double-stranded base portion and a single-stranded end portion; and a melting temperature of the double-stranded base portion is higher than a melting temperature for separating a double strand to be formed using the single-stranded end portion.

7. The molecule transfer and delivery system of claim 1, wherein the carrier molecule is a microtubule or an actin filament.

8. The molecule transfer and delivery system of claim 7, further comprising:

a patterned channel extending between the loading zone and the unloading zone, to which channel motor proteins are adsorbed;

wherein when the carrier molecule is the microtubule, the motor proteins are kinesins or dyneins.

9. The molecule transfer and delivery system of claim 7, further comprising:

a patterned channel extending between the loading zone and the unloading zone, to which channel motor proteins are adsorbed;

wherein when the carrier molecule is the actin filament, the motor proteins are myosins.

10. A molecule transfer and delivery system comprising:

a carrier molecule comprising a single-stranded towing nucleotide;

a cargo molecule comprising a molecule to be transferred or delivered and a single-stranded loading nucleotide which is longer than the single-stranded towing nucleotide and which is partially complementary to the single-stranded towing nucleotide;

an unloading nucleotide that is fully complementary to the single-stranded towing nucleotide;

a loading zone comprising means for contacting and hybridizing said carrier molecule and said cargo molecule to form a loaded carrier molecule; and an unloading zone comprising means for contacting and hybridizing said loaded carrier molecule with the unloading nucleotide to form a complex between the carrier molecule and the unloading nucleotide and an unloaded cargo molecule.

11. The molecule transfer and delivery system of claim 10, further comprising a channel extending between the loading zone and the unloading zone.

12. The molecule transfer and delivery system of claim 10, further comprising a patterned channel comprising motor proteins or kinesins extending between the loading zone and the unloading zone on a glass or plastic substrate produced by UV irradiation or direct drawing using an electron beam.

13. The molecule transfer and delivery system of claim 10, wherein the unloading nucleotide is bonded to a structure within the unloading zone.

14. The molecule transfer and delivery system of claim 10, wherein the carrier molecule is part of a microtubule or part of an actin filament.

15. A composition comprising:

an isolated or purified carrier molecule, which is capable of gliding on motor proteins, attached to a first single-stranded polynucleotide;

an isolated or purified target cargo molecule attached to a second single-stranded polynucleotide which is partially complementary to the first single-stranded polynucleotide;

a loading zone suitable for contacting the carrier molecule and the target cargo molecule and for partially hybridizing the first and second single-stranded polynucleotide;

a channel or flow path between the loading zone and an unloading zone to which an isolated or purified motor protein on which the carrier molecule glides is adsorbed; and an unloading zone to which a third single-stranded nucleotide having a higher binding affinity for the second single-stranded polynucleotide than does the first single-stranded polynucleotide is bonded.

16. The composition of claim 15, wherein the third single-stranded polynucleotide is fixed at the unloading zone and hybridizes to a portion of the second single-stranded polynucleotide that does not contribute to the formation of a double-strand with the first polynucleotide.

17. The composition of claim 15, wherein said carrier molecule is a microtubule carrier molecule and said motor protein is a kinesin or dynein; or wherein said carrier molecule is actin and said motor protein is myosin.

18. A method for transporting a cargo molecule comprising:

providing a carrier molecule that is capable of gliding on a motor protein and which is attached to a first single-stranded polynucleotide, contacting a cargo molecule that is attached to a second single-stranded polynucleotide that is partially complementary to the first single-stranded polynucleotide attached to the carrier molecule in a loading zone for a time and under conditions suitable for partial hybridization between the first and second single-stranded polynucleotides;

contacting the complex of the cargo molecule-first single-stranded polynucleotide and second single-stranded polynucleotide-carrier molecule with a channel or flow path between the loading zone and an unloading zone to which an isolated or purified motor protein on which the carrier molecule glides is adsorbed for a time and under conditions suitable for transport of said complex from the loading zone to the unloading zone; and contacting said complex at the unloading zone with a third single-stranded nucleotide that binds to the second single-stranded polynucleotide and displaces the first single-stranded polynucleotide attached to the carrier molecule;

thereby transporting the cargo molecule attached to the second single-stranded polynucleotide from the loading zone to the unloading zone.

* * * * *